(12) United States Patent
Sliwa et al.

(10) Patent No.: US 8,777,857 B2
(45) Date of Patent: Jul. 15, 2014

(54) SINGLE TRANSDUCER WITH ANGULAR ORIENTATION FOR LESION FEEDBACK IN ABLATION CATHETER

(75) Inventors: John Sliwa, Los Altos Hills, CA (US); Zhenyi Ma, San Jose, CA (US); Stephen Morse, Menlo Park, CA (US)

(73) Assignee: St. Jude Medical, Inc., St. Paul, MN (US)

( * ) Notice: Subject to any disclaimer, the term of this patent is extended or adjusted under 35 U.S.C. 154(b) by 204 days.

(21) Appl. No.: 13/086,605

(22) Filed: Apr. 14, 2011

(65) Prior Publication Data
US 2012/0265070 A1    Oct. 18, 2012

(51) Int. Cl.
    *A61B 8/00*    (2006.01)
(52) U.S. Cl.
    USPC .......................................... 600/439; 600/471
(58) Field of Classification Search
    USPC ............................................. 600/439, 471
    See application file for complete search history.

(56) References Cited

U.S. PATENT DOCUMENTS

| | | | | |
|---|---|---|---|---|
| 5,409,000 A | * | 4/1995 | Imran | 600/374 |
| 5,588,432 A | | 12/1996 | Crowley | |
| 5,651,366 A | * | 7/1997 | Liang et al. | 600/439 |
| 5,840,030 A | * | 11/1998 | Ferek-Petric et al. | 600/439 |
| 6,394,956 B1 | * | 5/2002 | Chandrasekaran et al. | 600/439 |
| 6,450,965 B2 | | 9/2002 | Williams et al. | 600/467 |
| 6,638,222 B2 | * | 10/2003 | Chandrasekaran et al. | 600/439 |
| 6,645,202 B1 | * | 11/2003 | Pless et al. | 606/41 |
| 8,057,465 B2 | | 11/2011 | Sliwa et al. | 606/27 |
| 2002/0099292 A1 | * | 7/2002 | Brisken et al. | 600/466 |
| 2002/0173784 A1 | * | 11/2002 | Sliwa et al. | 606/28 |
| 2003/0073992 A1 | * | 4/2003 | Sliwa et al. | 606/41 |
| 2005/0033274 A1 | * | 2/2005 | Pless et al. | 606/27 |
| 2008/0039746 A1 | * | 2/2008 | Hissong et al. | 601/3 |
| 2009/0131798 A1 | | 5/2009 | Minar et al. | |
| 2010/0168569 A1 | | 7/2010 | Sliwa et al. | |
| 2010/0168570 A1 | | 7/2010 | Sliwa et al. | |
| 2010/0168572 A1 | | 7/2010 | Sliwa et al. | |
| 2011/0160584 A1 | * | 6/2011 | Paul et al. | 600/439 |
| 2012/0165667 A1 | * | 6/2012 | Altmann et al. | 600/439 |

FOREIGN PATENT DOCUMENTS

| | | |
|---|---|---|
| EP | 1 554 986 A1 | 7/2005 |
| WO | 2010082146 A1 | 7/2010 |
| WO | 2010103423 A2 | 9/2010 |

OTHER PUBLICATIONS

M. Wright et al., "Real-time lesion assessment using a novel combined ultrasound and radiofrequency ablation catheter", Heart Rhythm, Feb. 2011, 9 pp., vol. 8, No. 2, Elsevier Inc.

* cited by examiner

*Primary Examiner* — Jonathan Cwern
(74) *Attorney, Agent, or Firm* — Wiley Rein LLP

(57) ABSTRACT

An ablation catheter comprises: an elongated catheter body extending along a longitudinal axis; at least one ablation element disposed in a distal portion which is adjacent the distal end of the catheter body to ablate a targeted tissue region outside the catheter body; a single pulse-echo ultrasonic transducer disposed in the distal portion and arranged to emit and receive an acoustic beam along a centroid in a beam direction, at a transducer angle of about 30-60 degrees relative to a distal direction of the longitudinal axis at a location of intersection between the longitudinal axis and the beam direction of the centroid of the acoustic beam; and a mechanism to manipulate the distal portion in movement including rotation of at least the distal portion around the longitudinal axis. The single ultrasonic transducer emits and receives acoustic pulses to provide lesion information in the targeted tissue region being ablated.

21 Claims, 4 Drawing Sheets

FIG. 4B  FIG. 4C

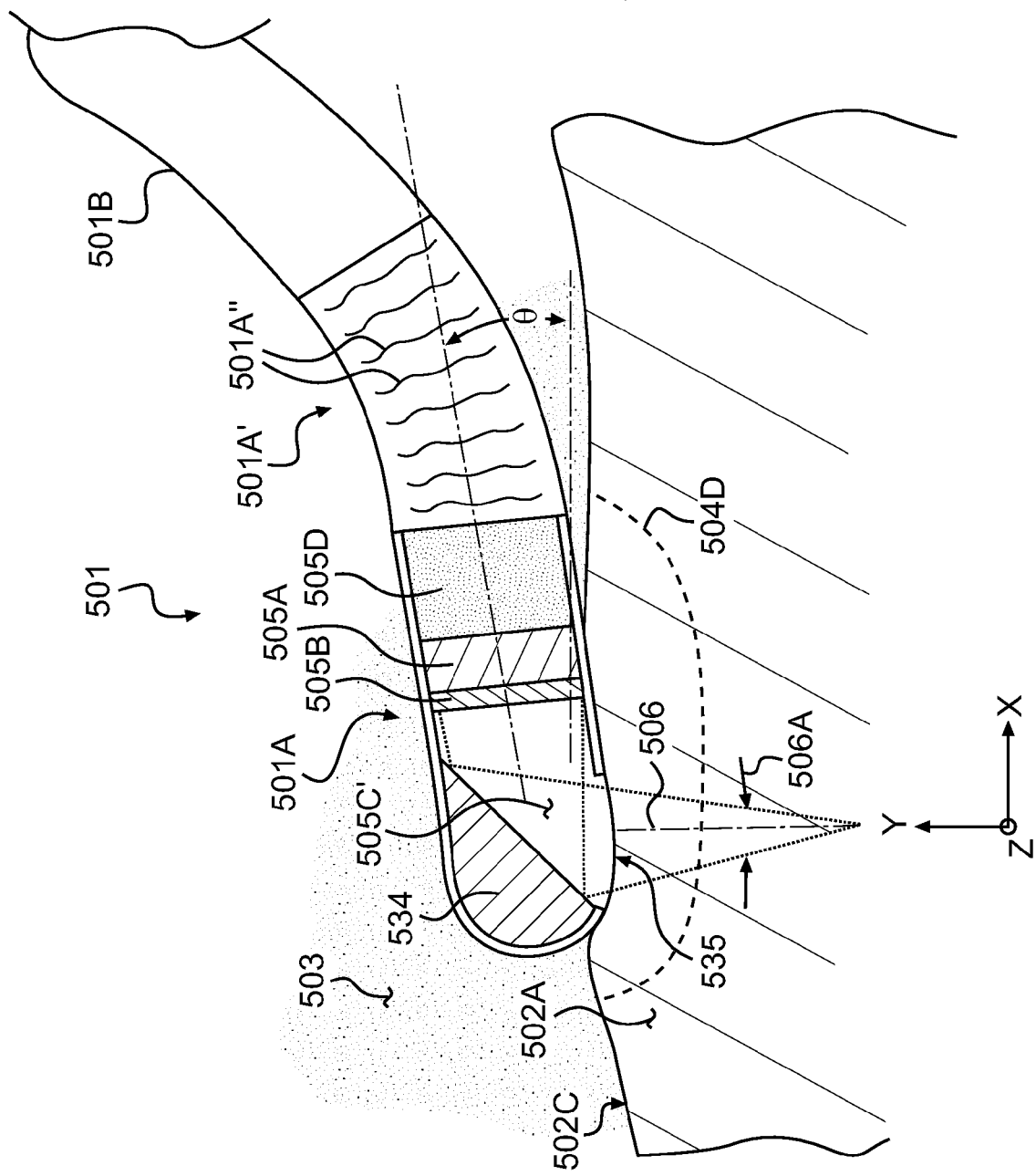

SINGLE TRANSDUCER WITH ANGULAR ORIENTATION FOR LESION FEEDBACK IN ABLATION CATHETER

BACKGROUND OF THE INVENTION

The present invention relates generally to ablation devices with acoustic or ultrasonic feedback and, more specifically, to a single ultrasonic transducer with an angular orientation for lesion feedback in an ablation catheter.

Current industry R&D in ultrasonic lesion feedback focuses on transducers that look out forwardly and sideways. This requires the use of dual transducers in an ablation instrument such as a catheter, resulting in a considerable expense and a significant loss of electrode tip metal for RF (radiofrequency) ablation or the like. Such an approach leads to an undesirably larger tip size to accommodate the two transducers or to poorer performing smaller (thinner) acoustic standoffs and/or backers for the dual transducers.

BRIEF SUMMARY OF THE INVENTION

Embodiments of the present invention provide a single transducer with an angular orientation for lesion feedback in an ablation catheter. As compared to the use of dual transducers, the single transducer configuration allows room for a thicker acoustic standoff/backer which gives the design superior shallow lesion ability and axially better resolution while still allowing operation over a wide range of tip-tissue contact angles.

In accordance with an aspect of the present invention, an ablation catheter comprises: an elongated catheter body extending longitudinally between a proximal end and a distal end along a longitudinal axis; at least one ablation element disposed in a distal portion which is adjacent the distal end of the catheter body to ablate a targeted tissue region outside the catheter body; a single pulse-echo ultrasonic transducer disposed in the distal portion and arranged to emit and receive an acoustic beam along a centroid in a beam direction, at a transducer angle of between about 30 degrees and about 60 degrees relative to a distal direction of the longitudinal axis at a location of intersection between the longitudinal axis and the beam direction of the centroid of the acoustic beam of the ultrasonic transducer; and a manipulation mechanism to manipulate the distal portion in movement including rotation of at least the distal portion around the longitudinal axis. The single pulse-echo ultrasonic transducer emits and receives acoustic pulses to provide lesion information in the targeted tissue region being ablated.

In some embodiments, the single pulse-echo ultrasonic transducer has an operating frequency of between about 3 megahertz and about 60 megahertz. The single pulse-echo ultrasonic transducer has a natural focus distance without a lens. The single pulse-echo ultrasonic transducer has at least one acoustic matching layer. The ablation catheter further comprises an attenuative backer material in the distal portion, wherein the single pulse-echo acoustic transducer is disposed between the attenuative backer material and the targeted tissue region. The single pulse-echo ultrasonic transducer comprises at least one of: a single crystal piezomaterial; a polycrystalline piezomaterial; a composite piezomaterial; a CMUT (capacitive micromechanical ultrasound transducer); a MEMS (microelectromechanical systems) based transducer; and a piezopolymer. The ablation catheter further comprises an acoustic lens disposed between the single pulse-echo ultrasonic transducer and the targeted tissue region. The ablation catheter further comprises an acoustic mirror redirecting the acoustic beam emitting from the single pulse-echo ultrasonic transducer so as to redirect the acoustic beam before its exiting from the distal portion. The acoustic mirror further focuses or defocuses the acoustic beam. The manipulation mechanism comprises a proximal catheter handle coupled with the catheter body and the distal portion. The transducer angle is fixed.

In specific embodiments, a part of the distal portion immediately surrounding the single pulse-echo ultrasonic transducer is rigid and another part of the distal portion is flexible so as to allow bending of the distal portion to reorient the ultrasonic transducer relative to the tissue surface and the catheter body while still being fixed relative to the immediately surrounding rigid part of the distal portion. The ablation catheter further comprises a plurality of lines coupled with the distal portion to deliver one or more of power to the at least one ablation element, irrigant to the distal portion, and steering control of the distal portion. The at least one ablation element disposed in the distal portion comprises an RF ablator electrode for contacting tissue within range of the transducer angle.

In accordance with another aspect of the invention, an ablation catheter comprises: an elongated catheter body extending longitudinally between a proximal end and a distal end along a longitudinal axis; at least one ablation element disposed in a distal portion which is adjacent the distal end of the catheter body to ablate a targeted tissue region outside the catheter body; a single pulse-echo ultrasonic transducer disposed in the distal portion and arranged to emit and receive an acoustic beam along a centroid in a beam direction, at a transducer angle of between about 30 degrees and about 60 degrees relative to a distal direction of the longitudinal axis at a location of intersection between the longitudinal axis and the beam direction of the centroid of the acoustic beam of the ultrasonic transducer; and means for manipulating the distal portion in movement including rotation of at least the distal portion around the longitudinal axis. The single pulse-echo ultrasonic transducer emits and receives acoustic pulses to provide lesion information in the targeted tissue region being ablated.

These and other features and advantages of the present invention will become apparent to those of ordinary skill in the art in view of the following detailed description of the specific embodiments.

BRIEF DESCRIPTION OF THE DRAWINGS

FIG. 4B shows a resulting recovered tissue lesion having a hemispherical shape; FIG. 4C shows a resulting recovered tissue lesion having a flattened pancake shape.

FIG. 5 is a partial sectional view of an RF ablation tip according to another embodiment of the invention.

DETAILED DESCRIPTION OF THE INVENTION

Figure 1:
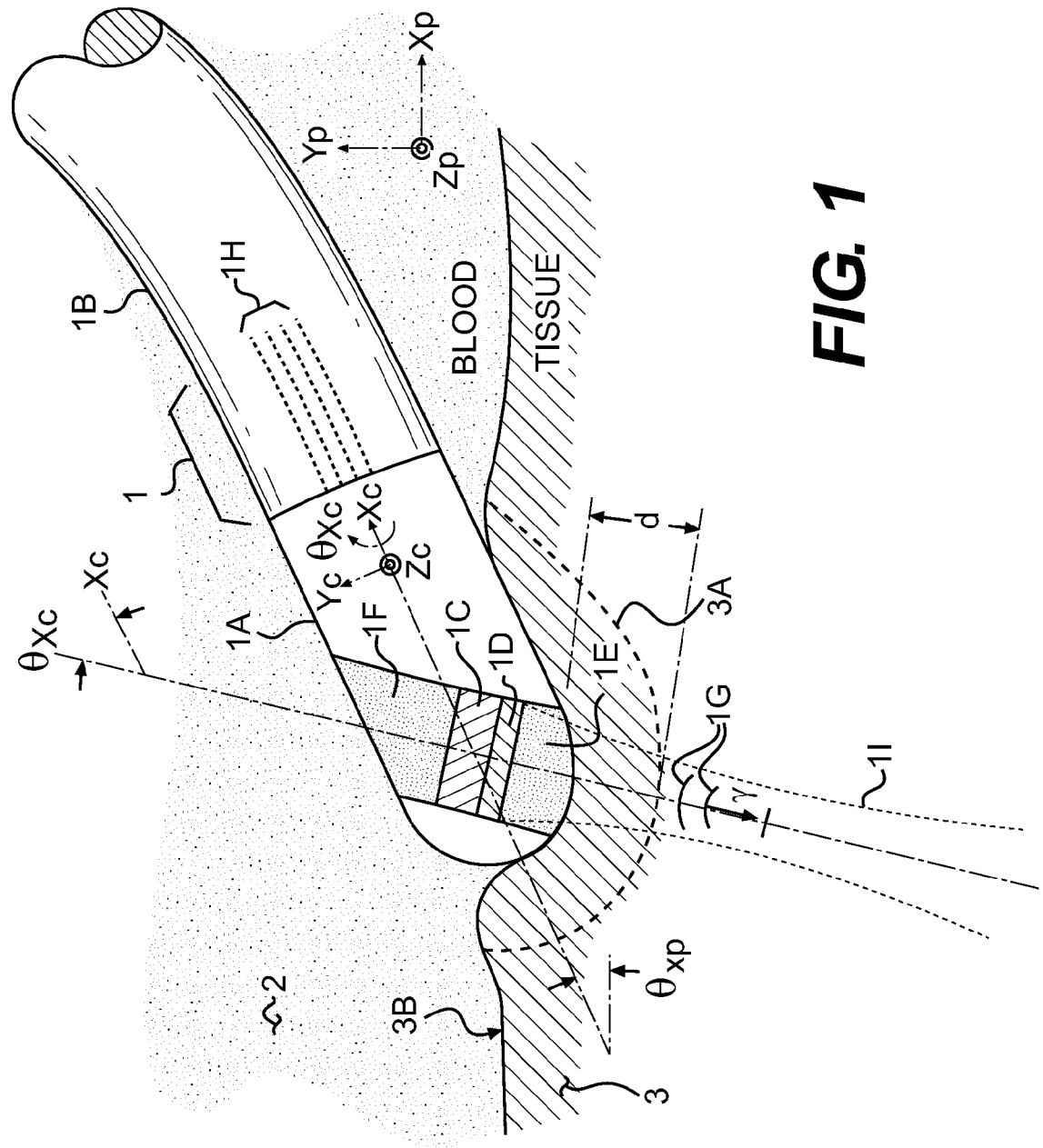
FIG. 1 is a partial sectional view of an RF ablation tip having a single transducer with an angular orientation for lesion feedback during tissue ablation according to one embodiment of the invention.

In the following detailed description of the invention, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment," "this embodiment," or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Exemplary embodiments of the invention, as will be described in greater detail below, provide ultrasonic feedback RF ablators and ablator tips and, more specifically, to a single ultrasonic transducer with an angular orientation to its surrounding RF electrode tip for lesion feedback in an ablation catheter. To be more specific, the transducer will always have an ultrasonic beam which itself has a centerline or centroid of beam peak intensity and sensitivity. The transducer angle to the ablator electrode tip refers to the angle between the local axial tip axis and the centroid or mid-region of the acoustic beam's cross section. This is an important distinction because an ultrasonic beam can itself have an angular width (positive angle diverging, negative angle converging, and focused) as opposed to being laser-like and non-expanding.

FIG. 1 shows an RF ablation electrode tip having a single ultrasonic transducer with an angular orientation for lesion feedback during tissue ablation. An RF ablation catheter 1 includes a distal ablating electrode tip 1a connected proximally to a catheter body 1b which is flexible and has one or more lumens. In this example, the catheter 1 is depicted immersed within a blood pool 2 for forming a lesion 3a in endocardial tissue 3. The thermal RF lesion 3a is formed on and into the tissue wall 3b by the catheter electrode RF tip 1a. A single ultrasonic transducer includes a piezomaterial 1c and preferably one or more acoustic matching layers 1d. The ultrasonic transducer is mounted in the tip 1a at a transducer beam centroid angle $\theta_{Xc}$, which is between about 30 and about 60 degrees, preferably about 45 degrees, relative to the forward direction of the tip longitudinal axis Xc of the tip 1. FIG. 1 shows the Cartesian coordinate system represented by Xc, Ye and Zc.

The entire catheter tip 1a is further depicted having a presentation to tissue (tissue contact) angle of $\theta_{Xp}$ relative to the endocardial wall 3b, which is horizontal along axis Xp in FIG. 1. FIG. 1 shows the Cartesian coordinate system represented by Xp, Yp, and Zp. The transducer 1c/1d emits and receives acoustic pulses 1g traveling at the tissue's approximate sonic velocity v of 1540 meters/sec along a beam envelope 1i. The acoustic waves 1g travel through the lesion 3a outwards and then back inwards as they are reflected. The lesion 3a has a depth d measured along the acoustic beam path or envelope 1i. Again we emphasize that the beam envelope 1i typically has a finite width which converges or diverges with distance from the transducer, but the beam will always have a centroid or central angle or sort of centerline with an angle $\theta_{Xc}$ to the axial tip axis.

It will be appreciated that if $\theta_{Xc}$ and $\theta_{Xp}$ are both 45 degrees, then the beam path 1i of the transducer 1c/1d will be oriented normally or at 90 degrees into the tissue 3b wall (along the −Yp axis). More typically though, $\theta_{Xc}$ will be fixed at an angle of about 45 degrees (typically between 30 and 60 degrees) and $\theta_{Xp}$ will be variable throughout an ablation procedure and will depend on how the catheter tip 1a is presented to the tissue wall 3b at that moment. The presentation angle of the electrode tip 1a to tissue $\theta_{Xp}$ can physically be from about 90 degrees (tip-normal) to about 0 degree (tip-parallel) depending on the lesions being made.

For a catheter tip 1a embedded or depressed into a tissue surface 3b (as shown in FIG. 1) and for a reasonably wide range of angles $\theta_{Xp}$ (the variable tip tissue contact angle), the detected lesion depth d is a good approximation of the maximum depth $d_{max}$ when $\theta_{Xc}$ (the fixed transducer angle) is fixed somewhere between about 30 and 60 degrees (preferably at about 45 degrees). Practitioners are typically interested in the maximum lesion depth for transmurality and in the lesion length or width insofar as being able to say adjacent lesions are continuous or abutted or not.

Despite this fairly good approximation capability, it is actually possible to do even better if one knows the actual real-time tissue contact angle $\theta_{Xp}$ at the moment of measurement. In that case, one can apply a correction factor, if worthwhile, to account for differences between the detected depth and the actual maximum depth based on bench studies done using that tip orientation. This correction factor corrects for the fact that the "depth" measured along the acoustic beam line will typically be slightly non-normal to tissue and may report a "depth" which is actually larger for flat pancake lesions (or even smaller for narrow deep lesions) than the real 90 degree penetration depth.

The tissue contact angle $\theta_{Xp}$, if it is desired for the most accurate result, can be determined or deduced in one or more of several ways and some of the more likely methods are described. While a useful product is readily possible even without such correction factors, a premium product may include the correction factor capability. Tissue contact angle ($\theta_{Xp}$) detection methods include the following three approaches:

1) The first is $\theta_{Xp}$ from an Ensite™ (http:/www.sjmprofessional.com/Products/US/Mapping-and-Visualization/EnSite-System.aspx) or Carto™ (http://www.biosensewebster.com/products/navigation/cartoxp.aspx) cardiac spatial navigation system based on computed or estimated tip angle to the graphically modeled endocardial surface. These systems already create three-dimensional (3-D) graphical displays of cardiac structures and arrhythmias and enable the spatial navigation of electrophysiology catheters in real time. Such systems already visually and mathematically provide the spatial orientation of the electrode tip and the spatial map and shape of the heart/tissue wall. By either simply observing the display where the RF electrode touches the wall and visually estimating the angle or by adding a simple angle computation utilizing the tip orientation and a computed local wall tangent derived from the wall model, one could obtain the tissue contact angle $\theta_{Xp}$.

2) Most modern catheters have radiopaque markers of gold or other heavy metal routinely used to discern in X-Ray fluoroscopy the position and orientation of a catheter tip such as 1a and sometimes even of a flexible lumen portion such as 1b. Using such conventional markers, the user can already visually discern the approximate tip orientation with respect to the contacting tissue and hence estimate the angle $\theta_{Xp}$. As is also widely known, one may additionally utilize an X-Ray contrast agent released into the blood from the catheter to enhance the outline of the blood filled chambers and the heart wall.

3) The third is the angle $\theta_{Xp}$ estimated from a force/angle sensor such as an Endosense™ force/angle sensor (www.endosense.com). Such catheter tips as that of Endosense's "Tacticath"® already report their contact angle and contact force for other purposes of obtaining reproducible ablations. By mounting our inventive transducer in such a tip, one thereby obtains the tissue contact angle $\theta_{Xp}$ as well as the tip contact force.

Figure 4A:
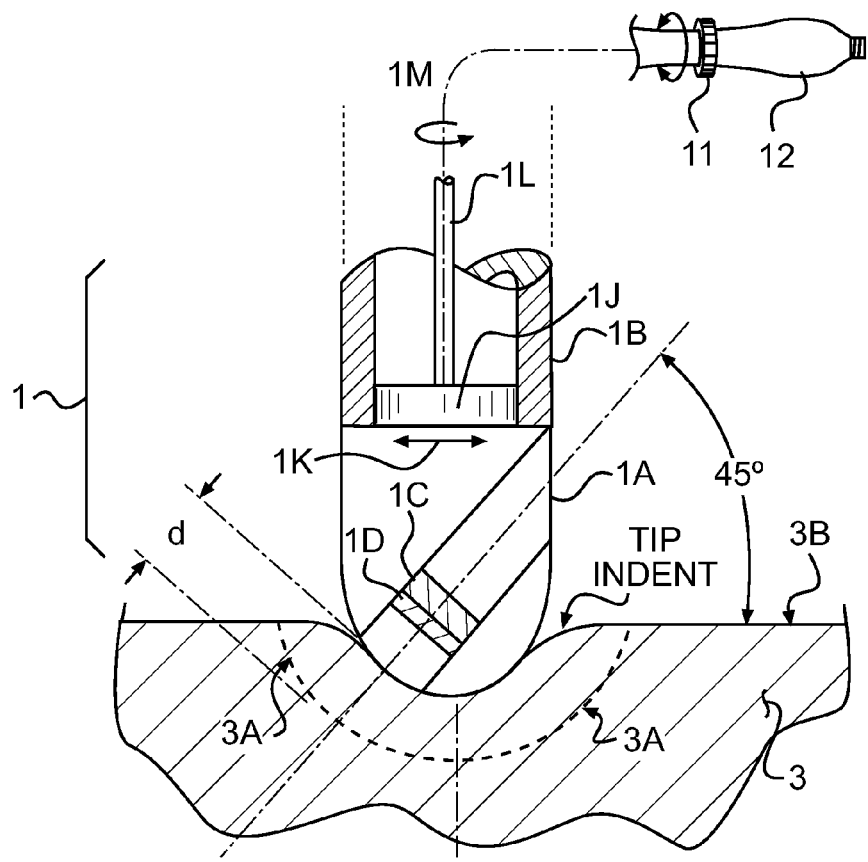
FIG. 4A is a partial sectional view of the ablation tip of FIG. 1 showing an example of a rotational mechanism for rotating the ablation tip and illustrating lesion shapes and depths in the tissue during and after ablation involving contact between the ablation tip and the tissue.
Figure 4D:
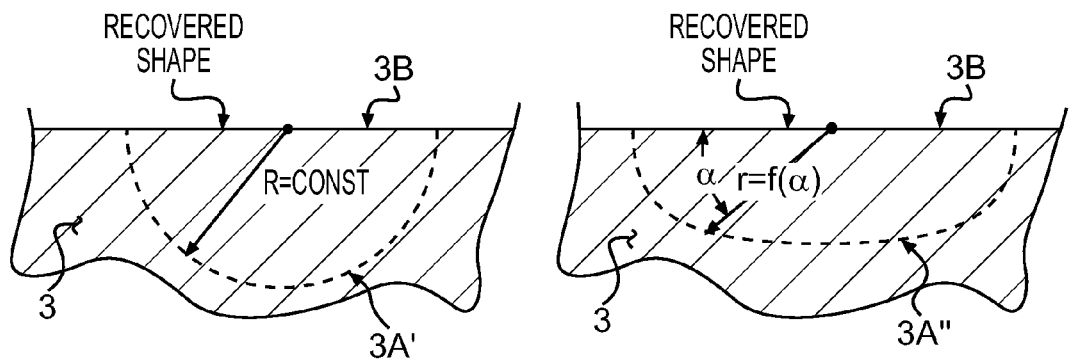
FIG. 4D illustrates a way to describe a lesion having a variable radius which is a function of at least one angle α measured with respect to a first reference line on the tissue surface.
Figure 4D:
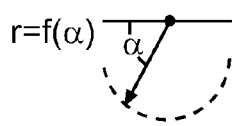

The actual tissue contact angle $\theta_{Xp}$ may be used to correct the ultrasonic lesion depth measurements but it is not always required. FIG. 4 is used to illustrate the reason a correction may be beneficial for maximum lesion-depth accuracy. FIG. 4A is a partial sectional view of the ablation tip of FIG. 1 showing an example of a rotational mechanism for rotating the ablation tip and illustrating lesion shapes and depths in the tissue during and after ablation involving contact between the ablation tip and the tissue. In FIG. 4A, the catheter tip 1a is oriented at about 90 degrees to the tissue surface 3b. The transducer 1c/1d and ultrasonic beam path are therefore oriented at about 45 degrees to the tissue surface 3b. The tissue is also typically somewhat indented by the pressing catheter tip 1a. A lesion 3a of depth d (measured in the indented state) as measured along the beam line has been formed by the tissue indenting tip. It will be apparent that, due both to the recovery of the indentation after the tip 1a is physically removed and the lesion's not necessarily having a constant radius (even as indented), the resulting recovered tissue lesion may have a shape ranging between hemispherical (FIG. 4B having lesion 3a') and a flattened pancake shape (FIG. 4C having lesion 3a"), for example. An RF lesion can sometimes, but more rarely, can even be deep and narrow (not shown). However we can generally describe the lesion in spherical or polar coordinates as having a variable radius which is a function of at least one angle α measured with respect to a first reference line on the tissue surface 3b (line on paper in FIG. 4C), i.e., r=f1(α), as seen in FIG. 4C and more generally in FIG. 4D. For a hemispherical lesion, the radius is r=constant. Lesions made near 90 degrees (FIG. 4A) are typically bodies of revolution and symmetrical to the tip 1a, whereas if the tissue contact angle $\theta_{Xp}$ leans over more toward 45 degrees or less, the lesion starts to become more asymmetrical and no longer a body of revolution as the tip sidewall also starts ablating tissue as well as some of the tip end. By making lesions at various tissue contact angles $\theta_{Xp}$, RF powers, times, and irrigant flow rates in the engineering development phase, one can determine the function f1(α) (FIG. 4C) for each such set of conditions. Such shape and size behavior data may be provided in or to the ablation catheter from lookup tables or by computational models operated resident on the ablation console or on a network, for example. Note that for an asymmetrical lesion, the lesion radius sampled across the orthogonal lesion length and width cross sections respectively will be a function of two angles f3(α, β), wherein β is measured with respect to a second reference line on the tissue surface 3b which is perpendicular to the first reference line (line into paper in FIG. 4C).

We show a 45 degree $\theta_{Xc}$ (transducer to tip angle) in FIGS. 1 and 4. We show a $\theta_{Xp}$ (tip to tissue angle) of about 30 degrees in FIG. 1 and 90 degrees in FIG. 4. The actual ultrasonic beam tissue penetration angle (actual tissue beam angle) relative to the tissue normal (ignoring signs) in FIG. 1 is about 15 degrees off normal (90−45−30=15) and in FIG. 4 is about 45 degrees off normal (90−45−90=−45).

Knowing the tissue beam angle (relative to the tissue normal) through a lesion made with a known tip orientation allows, based on prior lesion characterization during product development, the reporting of lesion radius across the two orthogonal planes or sections f1(α) and f2(β). It will be appreciated that f1(') and f2(β) are generally similar functions for the depicted 90 degree lesion but can be dissimilar functions or asymmetric for an ablating tip 1a at a lower than 90 degrees acute angle, as would be anticipated for an RF electrode making a "somewhat sideways" lesion. It will further be recognized then that even when the tip 1a takes various angles to the tissue surface 3b, as long as one knows the tissue contact angle $\theta_{Xp}$, then one can compute or "look up" the maximum depth of that lesion using f1(α) and f2(β) even though it may not occur directly in front of the transducer. Given the ultrasonically measured depth d along the angle α and the known tip orientation, one not only can describe the lesion shape as f1(α) and f2(β) but can also report its length, width, and/or estimated volume such as by assuming an ellipsoidal volume defined by the length, width, and depth. Again, we emphasize that these corrections are to obtain maximal accuracy and are not always necessary.

FIG. 1 shows that the transducer 1c/1d is stood-off from the deformed or indented tissue wall 3b by an acoustic standoff 1e which is an acoustic window material such as TPX, polystyrene, Ultem® (an unfilled polyetherimide), silicone, or even water or blood. This standoff 1e allows detection of shallow lesions of small depth d (e.g., in the 1 mm depth range or less) close to the transducer face despite known nearfield acoustic reverberations of tissue contacting transducers. Further, the transducer 1c/1d is acoustically and mechanically backed by an acoustic attenuation backer material if as is known for good quality pulse-echo transducers. High acoustic impedance backers typically contain epoxy or rubber and tungsten while low acoustic impedance backers typically contain epoxy and alumina or glass filler. Either would be highly attenuative as is known in the art, thereby attenuating the backwards propagating waves by about 20-40 dB. The attenuative backer material may further take a shape conducive to reflection minimization from its backside. Also depicted in FIG. 1 in the catheter lumen of the proximal catheter body 1b are interconnects and/or fluid or utility lines 1h. These lines 1h include, for example, saline irrigation, transducer electrode wires, RF ablation electrode leads, thermocouple/thermistor wires, tip steering wires, 3D spatial positioning sensor wires, and tip-rotation mechanisms/drives.

As mentioned above, the transducer typically and preferably has at least one acoustic matching layer, and at least one acoustic backer material entity. The transducer may utilize at least one of: a single crystal piezomaterial, a polycrystalline piezomaterial, a composite piezomaterial, a CMUT (capacitive micromechanical ultrasound transducer) or other MEMS (microelectromechanical systems) based transducer, and a piezopolymer as is known to the transducer arts. The ultrasonic transducer typically operates somewhere in the range of about 3 megahertz to about 60 megahertz, preferably about 6 megahertz to about 40 megahertz, and more preferably about 8 megahertz to about 25 megahertz. The transducer may have a natural focus distance without using any acoustic lens. Alternatively, an acoustic lens such as a spherical lens (or an acoustic focused or unfocused mirror) is provided for the transducer in the tip. As a lens example, the standoff 1e in FIG. 1 could also act to focus or defocus the beam as long as the material making up the standoff 1e has a velocity different from the velocity of the tissue and the interface between the lens/standoff and the tissue is curved as shown. For instance, a low attenuation unfilled epoxy 1e could serve as both a curved lens and a standoff, as is widely known in the art. Further examples include any lens causing the acoustic beam to have a desirable divergence or convergence angle or collimated zero-divergence/convergence angle, and any mirror at least redirecting the beam and possibly also, via use of a shaped nonflat mirror, causing the acoustic beam to have a desirable divergence or convergence angle or collimated zero-divergence/convergence angle.

The transducer mounting angle $\theta_{x_c}$ relative to its immediate surrounding RF electrode 1a is typically fixed, such as at the approximate 45 degree angle as shown in FIG. 1 for the rigid metal electrode tip 1a. In some embodiments, while the electrode tip 1a is preferably rigid in the region immediately around the transducer, the remaining portion of the tip 1a may be flexible, preferably bendably and/or axially flexible. This can be achieved, for instance, by lasering an array of circumferential or helical slots into the walls of a hollow tubular metal tip. See, e.g., U.S. Patent Application Publication No. 2010/0152731, which is incorporated herein by reference in its entirety. The transducer herein could be placed, for example, at the end of such a flexible metal ablator tip, thereby allowing tip-bending to reorient the transducer relative to the tissue (and relative to the catheter body 1b) while still being fixed relative to its immediately surrounding inflexible tip portion.

The transducer is used to make any one or more of the following acoustic measurements along and/or from the direction of the beam: lesion depth along the beam line, proximity to target tissue from a blood pool standoff position, detection of prepopping or popping related phenomenon, and detection of or proximity to anatomical targets to be avoided. As explained the measurement may then optionally be corrected using models or look-up tables for maximal accuracy. The ultrasonic transducer can be operated while RF ablation is active or inactive but preferably the transducer operates during multiple very short pauses in RF ablation (i.e., pinging is interleaved with ablation). "Very short" means short enough that significant tissue cooling does not occur, but pauses typically on the order of milliseconds to a fraction of a second. Typically tens if not hundreds or thousands of acoustic feedback detections are made over the period of a heartbeat. Some may be repeated to reduce signal noise. In one preferred case, ultrasonic measurements are time-interleaved with periods of RF ablation so as to monitor real-time ablating action. One may also or alternatively carry out before-lesioning and after-lesioning measurements to establish a reflection baseline. In specific situations, at least one acoustic detection is made in a timed relationship with a heartbeat or ECG signal. That is to say, for example, ultrasonic measurements are done preferably at least at the same point in the heartbeat for all heartbeats. Measurements may also be done throughout the heartbeat. During a given heartbeat cycle when tissues are moving, the tip-tissue contact angle $\theta_{x_p}$ and tip contact force will cyclically vary and angular variation can be taken into account by recognizing that the varying angles result in different detected depths for each such orientation.

The duty cycle of the ultrasonic transducer's operation is preferably less than about 20%, more preferably less than about 10%, and most preferably less than about 5%. In one embodiment, the on-time for an individual ultrasonic measurement period is equal to or less than a thermal time constant of the cooling tissue which assures that only minimal cooling takes place between the RF power-off and following RF power-on events. In other embodiments, the ultrasonic on-time is preferably less than about 0.15 seconds or 150 milliseconds, more preferably less than about 0.10 seconds or 100 milliseconds, and most preferably less than about 0.05 seconds or 50 milliseconds per individual measurement period during which one or more pulse-echo events take place.

The catheter body and/or tip may further include any one or more of the following known components: a thermistor or thermocouple, an irrigation lumen, a spatial position sensor (as for the prior mentioned Ensite™ or Carto™ systems), a contact-force sensor, part or all of a tip contact angle to tissue sensor of any type, a platinum, gold, or rhodium containing metallic electrode component or radiopaque member, and a metallic thin film or mesh electrode in an acoustic pulse-echo path. The thin film or mesh allows the face of the transducer itself also optionally to act as an ablating RF electrode.

Figure 2:
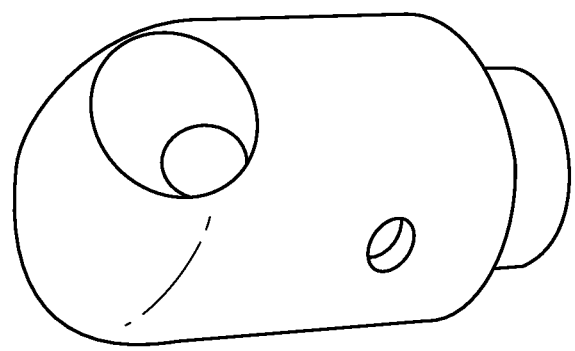
FIG. 2 is a perspective view of a 45 degree machined 7 French RF ablation tip to be used to house the single transducer of FIG. 1.
Figure 3:
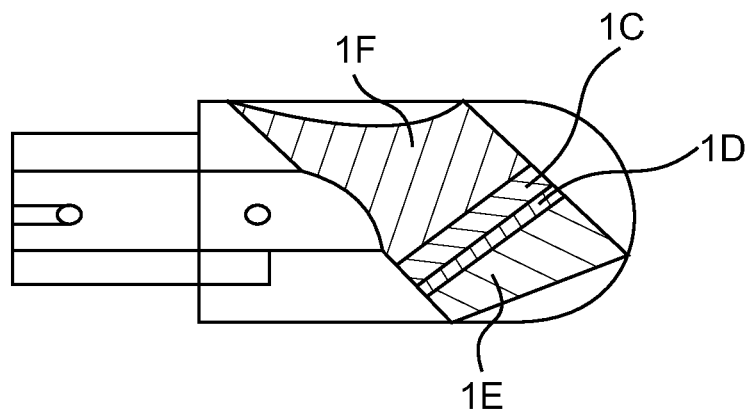
FIG. 3 is a partial sectional view of the ablation tip of FIG. 2.

An intrinsic advantage of the invention is that despite the tiny size of the catheter tip 1a (e.g., 7 French as shown in FIGS. 2 and 3), we can detect all lesions (tip-forward, tip-side, and in-between) and we can do so without substantially disrupting the ability of the remaining tip electrode material 1a to do ablation, conduct heat, and provide irrigant if desired. Further, the canted angle $\theta_{x_c}$ of the transducer relative to the tip allows for a thicker standoff 1e and a thicker backer if and at least a single matching layer 1d if not an even thicker double matching layer.

The metal electrode 1a is drilled out or provided with a bore to allow beam 1i passage and is filled with the transducer and the optional window or lens. If the standoff is electrically insulating, then that portion of the tip will not cause RF ablation. However, within the scope of the invention is the provision of a metal coated or otherwise electrically conductive ultrasonic component(s) such as the standoff, lens, or matching layer such that this drilled-out region still is capable of delivering RF ablation power even across the face of the standoff and/or lens. The inventors have found that even if the acoustic elements are not providing RF ablation, the nearby remaining tip metal periphery still forms a lesion similar to that of a standard non-drilled tip. The inventors believe that this is because as long as one has a circular donut-shaped electrode contact area to tissue, the RF current density at any appreciable depth is relatively unchanged. The tissue close to and immediately in front of the standoff/lens 1e is backfilled and sideways-filled with heat generated deeper in front of the tip and adjacently at the metallic periphery of the metallic hole in the tip.

The RF ablation catheter has a single ultrasonic pulse-echo transducer in the RF ablating tip used for pulse-echo lesion feedback. The transducer beam's centroid is oriented at approximately 30-60 degrees to the catheter tip longitudinal axis such that it has at least some view of lesions being made in any catheter-to-tissue orientation $\theta_{Xp}$. If the ultrasonic beam $1i$, for example, has a somewhat diverging beam within the lesioned region, then it "covers" a wider range of angles than a narrower beam for given transducer angle $\theta_{Xc}$ and tissue contact angle $\theta_{Xp}$ and will report an average lesion depth d for that divergent angle range. In general, the transducer beam can be divergent or convergent, and the beam still has the beam centroid around which it is divergent or convergent.

The catheter 1 (or catheter tip 1a alone) is preferably manually or automatically rotated about the Xc axis (FIG. 1) such that the transducer beam 1i faces the indented tissue 3b as directly (as near-normal) as possible for measurement of the lesion depth d along the beam 1i. This orientation also typically results in the maximum acoustic reflected energy from depth and the maximized signal/noise performance. Alternatively, one may measure the depth d at a variety of tip-to-tissue orientations during or after local lesioning is tentatively finished.

Referring again to FIG. 4A, the electrode tip 1a may be rotated relative to catheter body 1b such as upon a bearing member 1j. A rotational drive shaft 1l is used to rotate around the longitudinal axis in an axial rotational direction 1m to impart rotation 1k upon the tip 1a relative to the catheter body 1b. The drive shaft 1l could be replaced with an in-tip motor or some other in-tip powered actuator. Alternatively, and as widely known in the rotational catheter art, one may bodily rotate the entire catheter 1a/1b wherein the tip 1a does not rotate relative to the body 1b but is fixed relative to and rotates with the body 1b. Such bodily rotation is now routinely done by the practitioner manually rotating the catheter handle 12 using a rotational mechanism 11. As is also known, catheter 1 may be bodily rotated in that manner while residing in a stationary introducer surrounding sheath (sheath not shown) which provides a slippery bearing surface around the catheter 1 and may have its own steering wires. An advantage of the approach using the rotational bearing 1j of FIG. 4A is that one gets rotation without requiring a larger overall catheter diameter or French size. If one instead (or in addition) uses the sheath, then one now is introducing a larger sheath into the lumen and may be more restricted in access.

FIG. 5 is a partial sectional view of an RF ablation tip according to another embodiment of the invention, wherein the transducer itself is forward pointing but its beam is redirected sideways by an acoustic mirror before its exit from the ablation tip. An RF ablation catheter 501 includes a distal ablating electrode tip 501a connected proximally to a catheter body 501b which is flexible and has one or more lumens. The catheter 501 has two metallic parts: a rigid part 501a and a flexing part 501a' having flexure slots 501a". In this example, the catheter 501 is depicted immersed within a blood pool 503 for forming a lesion 504d in endocardial tissue 502a. The thermal RF lesion 504d is formed on and into the tissue wall 502c by the catheter electrode RF tip 501a. A single ultrasonic transducer includes a piezomaterial 505a, and preferably one or more acoustic matching layers 505b and an acoustic backer 505d.

The ultrasonic transducer is mounted in the tip 501a in any desired orientation including, for example, a forward facing direction emitting a beam along the distal direction X of the tip 501 as shown in FIG. 5. Note that the tip 501a contains an acoustic mirror 534 which is configured to redirect the outgoing and incoming beam at an angle (e.g., 90 degrees) relative to the longitudinal tip axis. Disposed in the acoustic path between the mirror 534 and the transducer 505b,a,d is saline 505c'. The saline 505c' serves as an acoustic standoff from the tissue surface 502c such that the first couple of millimeters of tissue depth can be seen without interfering transducer ringdown artifacts. The mirror 534 would likely be made of stainless steel or tungsten but could alternatively be made of an air-like material such as a glass microballoon filled epoxy. A tip aperture or orifice 535 is provided at the beam path 506/506a such that the acoustic beam does not collide with the tip housing. Presuming the tip 501a is an RF ablation electrode, and the tip container or shell would likely be formed of metal such as platinum-iridium in the known manner. In FIG. 5, the aperture or beam orifice 535 is an open hole. In this manner, saline pumped into the tip cavity 505c' exits the orifice 535. Some smaller amount of saline may exit small laser-drilled holes (not shown) separate from the orifice 535. Note that by having the majority of the saline exiting the tip orifice 535, the tip electrode around the orifice is well-cooled despite its having a high RF-current density around its orifice perimeter. Further, the emanating saline serves to acoustically couple the transducer to the tissue and prevents bubbles from becoming trapped in or near the tip cavity 505c' or aperture 535. The inventors specifically note that if one monitors the water pressure being applied to the tip 501a from outside the patient, one can easily tell when the aperture 535 (and therefore the acoustic beam) is facing the tissue squarely because the back-pressure increases when the aperture is sealed against the tissue. This pressure monitoring technique can be employed manually to achieve automatically tip-aiming and can be done so independently or in combination with observing the actual acoustic pinging feedback. The acoustic mirror 534 may, for example, have an angle of 45 degrees resulting in a 90 degree beam exit (as shown), or a different angle such as 22.5 degrees resulting in a 45 degree beam exit (not shown). The mirror thickness need only be thick enough to provide adequate reflection (e.g., 95% or better); for metals, this is actually quite thin, i.e., on the order of microns in thickness. For manufacturing convenience, the mirror 534 can be thicker and all metal as shown in FIG. 5, or alternatively could comprise micromolded polymer having a thin-film metallic coating.

In making lesions with the inventive feedback tip, the user ultrasonically detects lesion features comprising both microbubbles caused by RF heating and inherent heated tissue features such as cells, tissue or muscle layers, and underlying lumens. The inventors have found that that the tip irrigant flow rate can suppress microbubbling in the shallow nearfield while allowing it more deeply in the heated tissue. The reason is that microbubbles do not appreciably appear until the temperature is over about 50° C. and more so at about 60° C., yet some lesion formation (necrosis) still occurs as long as the tissue temperature is above about 47° C. Thus this provides a mechanism, if desired, to suppress nearfield bubbles such that farfield bubbles are more easily acoustically visualized. It should be apparent that seeing farfield bubbles is virtually a guarantee that the nearfield tissue is ablated even if it did not get hot enough to bubble. One might even vary the irrigant (e.g., saline) flow rate such that nearfield bubbles are suppressed by high cooling flow rate earlier in the ablation to maximize visibility of deeper bubbles and then after that flow rate is decreased such that nearfield bubbles appear as well guaranteeing that nearfield tissue is certainly ablated. The inventors utilize a high flow rate of saline of about 17 ml/minute and low flow rates of about 2-8 ml/minute as an example. The inventors have found that they can operate their ablation device and system in a manner wherein a user or the system itself monitors the reflected signals at various depths before and during ablation and adjusts the RF power and/or irrigant coolant flow rate, such that deeper lesioning takes place away from the cooling irrigant while avoiding nearer surface tissue popping where the power density is higher. As necessary for certainty one can then purposely cause nearfield bubbles to assure shallow lesioning by reducing power and cooling and still assure no tissue pops. It was found that tissue popping, which is to be avoided, has warning signs such as rapid nearfield appearance of high contrast reflections. The system can use this observation to quickly start reducing power somewhat for example (before the pop can happen). All of the above monitoring and control can be done in a software algorithm. The user may still set nominal powers, irrigant flows, maximum tip temperature, and time, but such an algorithm can always assure one gets adequate lesioning yet avoids popping by its making its own prioritized adjustments during the lesioning process.

In accordance with an aspect of the invention, a method of providing lesion and anatomy feedback during catheter-based lesion ablation procedures comprises providing an ablation catheter having a distal ablating tip with a longitudinal axis, an intermediate flexible catheter lumen, and a proximal control handle or manipulator ("manipulator" covers use of a robot) to manipulate the tip. The distal tip contains an ultrasonic pulse/echo transducer having an acoustic beam which emanates from at least a portion of said distal tip at an angle to said longitudinal axis of the surrounding tip portion of between about 30 and 60 degrees. The transducer is operated in pulse-echo mode to provide reflective acoustic signals from one or more of nearby or contacting tissue, forming or formed lesions or underlying anatomy. The procedure benefits in efficacy or safety from the feedback.

In some embodiments, a lesion depth measured along an acoustic beam tissue-penetration direction is detected, reported to, or utilized by a user or an ablation control system. Either the detected depth itself is reported to or provided to either of the user or to an ablation control system, or the detected depth plus a detected tip-tissue contact angle are employed together to look up or model a different lesion dimension such as a maximum lesion depth, lesion width, or lesion volume. A tip irrigant flow rate is set to thermally control the runaway formation of microbubbles in any lesion region, most particularly in the shallow nearfield. The combination of irrigant flow rate and power is purposely chosen to suppress runaway microbubble formation in the nearfield but not to completely suppress microbubbles in the farfield such that the farfield microbubbles are more clearly visible and indicative of deeper lesioning. Following the previous step, the irrigant flow rate and possibly the power are then reduced to allow controlled microbubble formation in the nearfield. A state of microbubble formation in tissue detected by an acoustic transducer as an intensity of reflection in dB can thereby be taken to indicate certain necrosis. Any transducer can easily be calibrated during development such that one knows the reflective intensity correlating to microbubbling. It is rather obvious when microbubbling starts as the reflections appear and then grow more intense to the point of all the signals being reflected from the bubble cloud just before a large pop when the cloud coalesces and the tissue tears. During an ablation, the user preferably causes the state of microbubbles to appear in all regions of the desired lesion at at least some point during the formation of said lesion. Nearfield microbubble formation is suppressed by a tissue-cooling tip irrigant flow rate such that microbubble formation may be observed at greater depth indicative of lesioning or necrosis at the greater depth, the irrigant flow rate thereafter being reduced, possibly together with power, to then also allow nearfield microbubbles absolutely verifying nearfield lesioning or necrosis.

In accordance with another aspect of the invention, a method of providing lesion and anatomy feedback during or in support of catheter-based lesion ablation procedures comprises providing an ablation catheter having a distal ablating tip with a longitudinal axis, an intermediate flexible catheter lumen and a proximal control handle or manipulator. The distal electrode tip has a bendably flexible portion. The most distal and likely inflexible electrode tip portion contains an ultrasonic pulse/echo transducer having an emanating acoustic beam which emanates from at least a portion of said distal tip at an angle between about −180 and +180 degrees relative to the immediately surrounding tip portion longitudinal axis, more preferably between about +30 and +60 degrees and between about −30 and −60 degrees. The bendable electrode tip portion of the flexible tip is bendable to thereby present the emanating beam from the adjacent and most distal and likely inflexible tip portion to target tissue at a favorable penetration angle. It will be recognize that a flexed or bent tip as viewed in x-ray or fluoroscopy is an assurance of a minimum tissue contact force which can assure both good RF electrical contact and good acoustic contact. The transducer is operated in pulse-echo mode to provide reflective acoustic signals from one or more of nearby or contacting tissue, forming or formed lesions, or underlying anatomy. The procedure benefits in efficacy or safety from the feedback In specific embodiments, either ablation induced microbubbles at a tissue location are taken to indicate lesioning or necrosis is complete at that location, or an irrigant flow is set high enough relative to RF power to suppress microbubbles in the nearfield via surface cooling at least for a period in order to better see microbubbles at greater depths.

In the description, numerous details are set forth for purposes of explanation in order to provide a thorough understanding of the present invention. However, it will be apparent to one skilled in the art that not all of these specific details are required in order to practice the present invention. Additionally, while specific embodiments have been illustrated and described in this specification, those of ordinary skill in the art appreciate that any arrangement that is calculated to achieve the same purpose may be substituted for the specific embodiments disclosed. For example, the tip electrode may also serve as a sensing or pacing electrode. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. An ablation catheter comprising:
   an elongated catheter body extending longitudinally between a proximal end and a distal end along a longitudinal axis; and
   a distal ablating electrode which is adjacent the distal end of the catheter body to ablate a targeted tissue region outside the catheter body;
   a single pulse-echo ultrasonic transducer disposed in an interior space of the distal ablating electrode and arranged to emit from the interior space to an exterior of the distal ablating electrode and receive from the exterior to the interior space of the distal ablating electrode, an acoustic beam along a centroid in a beam direction, at a transducer angle of between about 30 degrees and about 60 degrees relative to a distal direction of the longitudinal axis at a location of intersection between the longitudinal axis and the beam direction of the centroid of the acoustic beam of the ultrasonic transducer; and a manipulation mechanism to manipulate the distal ablating electrode in movement including rotation of at least the distal ablating electrode around the longitudinal axis;

wherein the single pulse-echo ultrasonic transducer emits and receives acoustic pulses to provide lesion information in the targeted tissue region being ablated.

2. The ablation catheter of claim 1,
wherein the single pulse-echo ultrasonic transducer has an operating frequency of between about 3 megahertz and about 60 megahertz.

3. The ablation catheter of claim 1,
wherein the single pulse-echo ultrasonic transducer has a natural focus distance without a lens.

4. The ablation catheter of claim 1,
wherein the single pulse-echo ultrasonic transducer has at least one acoustic matching layer.

5. The ablation catheter of claim 1, further comprising:
an attenuative backer material in the interior space of the distal ablating electrode;
wherein the single pulse-echo acoustic transducer is disposed between the attenuative backer material and the targeted tissue region.

6. The ablation catheter of claim 1, wherein the single pulse-echo ultrasonic transducer comprises at least one of:
a single crystal piezomaterial;
a polycrystalline piezomaterial;
a composite piezomaterial;
a CMUT (capacitive micromechanical ultrasound transducer);
a MEMS (microelectromechanical systems) based transducer; and
a piezopolymer.

7. The ablation catheter of claim 1, further comprising:
an acoustic lens disposed between the single pulse-echo ultrasonic transducer and the targeted tissue region.

8. The ablation catheter of claim 1, further comprising:
an acoustic mirror redirecting the acoustic beam emitting from the single pulse-echo ultrasonic transducer so as to redirect the acoustic beam before its exiting from the distal ablating electrode.

9. The ablation catheter of claim 8,
wherein the acoustic mirror further focuses or defocuses the acoustic beam.

10. The ablation catheter of claim 1,
wherein the manipulation mechanism comprises a proximal catheter handle coupled with the catheter body and the distal ablating electrode.

11. The ablation catheter of claim 1,
wherein the transducer angle is fixed.

12. The ablation catheter of claim 1,
wherein a part of the distal ablating electrode immediately surrounding the single pulse-echo ultrasonic transducer is rigid and another part of the distal ablating electrode is flexible so as to allow bending of the distal ablating electrode to reorient the ultrasonic transducer relative to the tissue surface and the catheter body while still being fixed relative to the immediately surrounding rigid part of the distal ablating electrode.

13. The ablation catheter of claim 1, further comprising:
a plurality of lines coupled with the distal ablating electrode to deliver one or more of power to the ablating electrode, irrigant to the distal ablating electrode, and steering control of the distal ablating electrode.

14. The ablation catheter of claim 1,
wherein the distal ablating electrode comprises an RF ablator electrode for contacting tissue within range of the transducer angle.

15. The ablation catheter of claim 1,
wherein the distal ablating electrode is rigid in a region immediately around the ultrasonic transducer and a remaining portion of the distal ablating electrode is flexible.

16. An ablation catheter comprising:
an elongated catheter body extending longitudinally between a proximal end and a distal end along a longitudinal axis; and
a distal ablating electrode which is adjacent the distal end of the catheter body to ablate a targeted tissue region outside the catheter body;
a single pulse-echo ultrasonic transducer disposed in an interior space of the distal ablating electrode and arranged to emit from the interior space to an exterior of the distal ablating electrode and receive from the exterior to the interior space of the distal ablating electrode, an acoustic beam along a centroid in a beam direction, at a transducer angle of between about 30 degrees and about 60 degrees relative to a distal direction of the longitudinal axis at a location of intersection between the longitudinal axis and the beam direction of the centroid of the acoustic beam of the ultrasonic transducer; and
means for manipulating the distal ablating electrode in movement including rotation of at least the distal ablating electrode around the longitudinal axis;
wherein the single pulse-echo ultrasonic transducer emits and receives acoustic pulses to provide lesion information in the targeted tissue region being ablated.

17. The ablation catheter of claim 16, wherein the single pulse-echo ultrasonic transducer comprises at least one of:
a single crystal piezomaterial;
a polycrystalline piezomaterial;
a composite piezomaterial;
a CMUT (capacitive micromechanical ultrasound transducer);
a MEMS (microelectromechanical systems) based transducer; and
a piezopolymer.

18. The ablation catheter of claim 16, further comprising:
an acoustic lens disposed between the single pulse-echo ultrasonic transducer and the targeted tissue region.

19. The ablation catheter of claim 16, further comprising:
an acoustic mirror redirecting the acoustic beam emitting from the single pulse-echo ultrasonic transducer so as to redirect the acoustic beam before its exiting from the distal ablating electrode.

20. The ablation catheter of claim 19,
wherein the acoustic mirror further focuses or defocuses the acoustic beam.

21. The ablation catheter of claim 16,
wherein a part of the distal ablating electrode immediately surrounding the single pulse-echo ultrasonic transducer is rigid and another part of the distal ablating electrode is flexible so as to allow bending of the distal ablating electrode to reorient the ultrasonic transducer relative to the tissue surface and the catheter body while still being fixed relative to the immediately surrounding rigid part of the distal ablating electrode.

* * * * *